(12) United States Patent
Gideon et al.

(10) Patent No.: US 12,011,314 B2
(45) Date of Patent: Jun. 18, 2024

(54) BIOFEEDBACK APPARATUS AND METHOD

(71) Applicants: Eric Gideon, San Rafael, CA (US);
Benjamin Gideon, San Rafael, CA (US)

(72) Inventors: Eric Gideon, San Rafael, CA (US);
Benjamin Gideon, San Rafael, CA (US)

(*) Notice: Subject to any disclaimer, the term of this patent is extended or adjusted under 35 U.S.C. 154(b) by 0 days.

(21) Appl. No.: 18/126,629

(22) Filed: Mar. 27, 2023

(65) Prior Publication Data

US 2023/0320691 A1 Oct. 12, 2023

Related U.S. Application Data

(60) Provisional application No. 63/324,268, filed on Mar. 28, 2022.

(51) Int. Cl.
*A61B 7/04* (2006.01)
*A61B 5/00* (2006.01)
*A61B 7/02* (2006.01)
*A61B 5/024* (2006.01)

(52) U.S. Cl.
CPC .............. *A61B 7/04* (2013.01); *A61B 5/7225* (2013.01); *A61B 5/7289* (2013.01); *A61B 5/742* (2013.01); *A61B 7/026* (2013.01); *A61B 5/024* (2013.01); *A61B 2560/0443* (2013.01); *A61B 2562/0204* (2013.01); *A61B 2562/04* (2013.01); *A61B 2562/168* (2013.01)

(58) Field of Classification Search
CPC .. A61B 7/00; A61B 7/02; A61B 7/003; A61B 7/04
See application file for complete search history.

(56) References Cited

U.S. PATENT DOCUMENTS

| | | | | |
|---|---|---|---|---|
| 4,850,023 | A * | 7/1989 | Yarush | A61B 7/04 381/67 |
| 5,492,129 | A * | 2/1996 | Greenberger | A61B 7/04 600/528 |
| 5,931,792 | A * | 8/1999 | Packard | A61B 7/026 600/528 |
| 5,959,261 | A * | 9/1999 | Abelson | A61B 7/02 181/131 |
| 6,236,862 | B1 * | 5/2001 | Erten | H04B 1/123 455/501 |
| 2019/0365327 | A1 * | 12/2019 | Verkaik | A61B 5/6876 |

* cited by examiner

*Primary Examiner* — Michael J D'Abreu
(74) *Attorney, Agent, or Firm* — Staniford Tomita LLP

(57) ABSTRACT

A modular stethoscope system has multiple ear pieces and chest pieces. The modular stethoscope system allows multiple peoples' heartbeat and breathing sounds to be shared. The apparatus can have multiple heart modules that are placed on users' chests that can each receive circulatory and/or respiratory audio signals from the users. The heart modules can be coupled to each other and/or coupled to multiple audio output devices so that some or all of the users can hear the combined heartbeats. The heart modules' inputs and outputs can be shared through direct physical links and/or converted into electrical or wireless signals that can be received by other electrical audio output devices so that multiple users can listen to multiple heartbeat outputs.

8 Claims, 12 Drawing Sheets

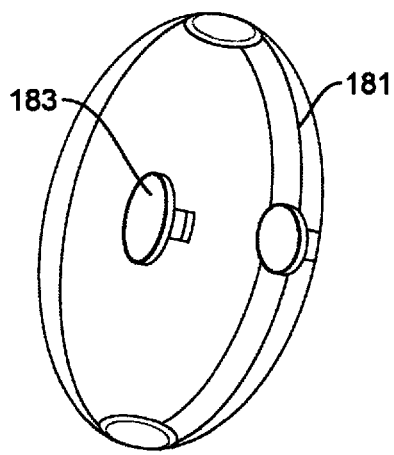
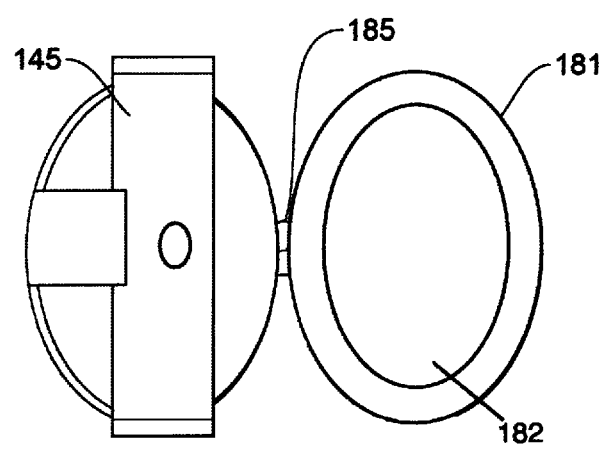
FIG. 11A  FIG. 11B
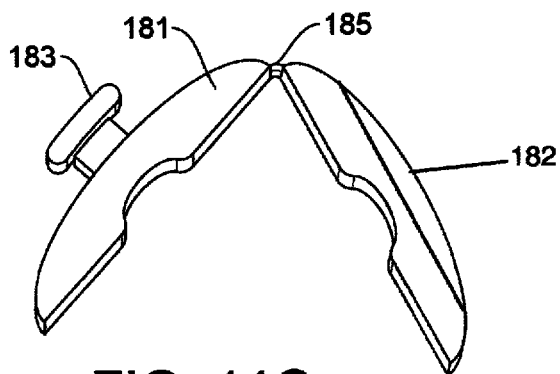
FIG. 11C
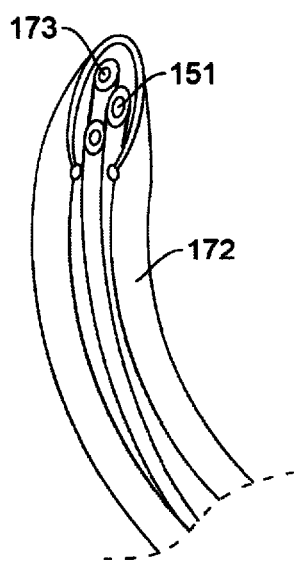
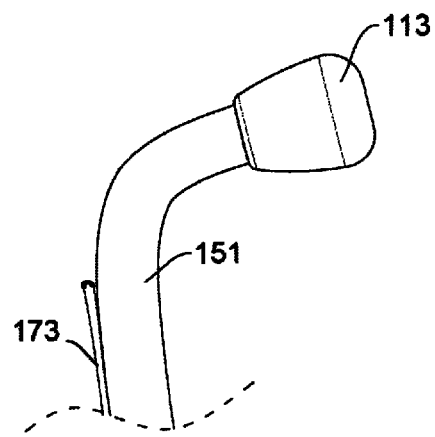
FIG. 12  FIG. 13

BIOFEEDBACK APPARATUS AND METHOD

CROSS-REFERENCE TO RELATED APPLICATIONS

This application claims priority to U.S. Provisional Patent Application No. 63/324,268, titled "Biofeedback Apparatus and Method" filed Mar. 28, 2022 which is hereby incorporated by reference in its entirety.

TECHNICAL FIELD

The present invention relates generally to stethoscopes and related auscultation devices, and more particularly to an improved biofeedback device enabling meditation techniques, alternative therapy, and social interaction based on the sounds of the heartbeat.

SUMMARY OF THE INVENTION

The present invention is biofeedback device that provides an acoustically based, stethoscope-styled biofeedback apparatus that can be used for entertainment, relaxation, meditation, and other medical purposes. The stethoscope apparatus can include a wishbone shaped headset that has ear pieces that are connected with tubing to a heart module that can include a chest piece and a diaphragm. The headset can be made of soft materials that form a low profile, adjustable, and bendable ergonomic structure. The headset can be made in a molded process. The inventive apparatus can allow a host user who is wearing the device to hear their own circulatory and/or respiratory sounds that can include heartbeats, breathing, bowel, and other body sounds. This device can be worn throughout the day and slept with to hear one's vitals while asleep, in the manner of subconscious meditation.

The inventive apparatus can have coupling connections that can allow multiple headsets to receive the auscultation sounds. In some embodiments, a single user's circulatory and/or respiratory output can be shared with multiple people. In a single user output to multiple listener configuration, the apparatus can have a multiple headset configuration so the user can share their auscultation sounds. The circulatory and/or respiratory output from the apparatus can be shared through a direct physical link via a conduit such as flexible tubing and/or converted into electrical or wireless signals that can be received by receivers and convened into audio signals by connected audio output devices. This signal transmission can allow multiple users to listen to one or more user's circulatory and/or respiratory sounds.

In other embodiments, multiple peoples' heartbeat and breathing outputs can be shared with multiple people. In these configurations, the apparatus can have multiple heart modules that are placed on users' chests that can each receive circulatory and/or respiratory audio signals from the users. The heart modules can be coupled to each other and also coupled to multiple audio output devices so that some or all of the users can hear the combined heartbeats. The heart modules' inputs and outputs can be shared through direct physical links and/or converted into electrical or wireless signals that can be received by other electrical audio output devices so that multiple users can listen to multiple heartbeat outputs.

In some embodiments, a microphone can be coupled to the apparatus to receive and possibly record the audio hear beat sounds. The superimposed user heartbeat sounds may be recorded or transmitted live to listeners via wired or wireless electrical connections. In these embodiments, the microphone coupled to a heart module can convert the heartbeat and possibly breathing sounds into electrical signals. The heartbeat electrical signals can be amplified and transmitted to a wired or wireless transmitter. Receivers can receive the heartbeat and possibly breathing sounds electrical signals that can be amplified and transmitted to audio output devices that can be worn and/or heard by one or more system users who can be in the immediate area or remotely located.

As discussed, the present invention can have various configurations and the integration of a microphone with electrical signals can allow for more flexibility in both design and use. Examples of different apparatus configurations may include but are not limited to:

1) A two user configuration for sharing one on one live sounds. In this embodiment, a couple or friends can share a heart moment, meditating, recreation, or a getting to know each other exercise. In some embodiments, these heartbeat signals can be shared electronically via a dating site or other social networking site.

2) In some embodiments, the electronic heartbeat can be used in a random search where social media can be used to detect and find a like-minded person to share heartbeat and breathing activities. The social media system can provide beating breathing hyperlink or other computer internet uniform resource locator (URL) to other users who may be in a local vicinity. This embodiment can function like a treasure hunt for other heartbeat sound sharing enthusiasts.

3) The present invention can be used in a large group setting with a leader's host heartbeat being broadcast to other guest users so they may all listen to and synchronize their heartbeats and/or breathing with a group leader or host. This configuration can be useful when a popular host such as the Dali Lama would like to meditate with a large 1,000+ person group.

4) In an embodiment, the heartbeat can be recorded and processed by a processor to determine a mean or average vital sound may be calculated and then the average vital sounds such as average heartbeat rate and amplitude can be broadcast to a group of system users, so as a group may synch their heartbeats and move their breathing rate together in a progressive direction.

5) In other embodiments, the vibrational frequency of each user's heartbeat may be calculated and converted into an electronic signal. The electrical signal from the users' heartbeats can then be synthesized by a processor or through any variety of crystal (e.g., rose quartz) to produce a personal audio tone or "song." The personal audio tone or song can be overlaid over a user's own unaltered vital sign chest sounds such as the heartbeat as an audio prompt or cue. Thus, the system can allow a user to incorporate an audio song so one may compose the personal audio tone. This personal audio tone can be used as a sound for adjusting one's vitals, i.e., a personal soundtrack. These personal audio tone songs may also be linked to the personal audio tone songs of others with or without the other vital sounds.

6) In some embodiments, the described group audio methods can be used to create group sounds such as Gregorian chants or holy sounds. The system can be used as an audio effect similar to the "Marco Polo" children's game where group audio sound volume can be electronically adjusted in volume to get louder as a system user's heartbeat approaches the target heartbeat rate or get fainter recede as the system user's heartbeat deviates more from their optimum heartbeat and/or breathing rates. In these embodiments, a processor can determine the target heartbeat and/or breathing rates and can then the system can monitor the heartbeat and/or breathing rates of other system users who are attempting to synchronize heartbeat and/or breathing rate with target heartbeat and/or breathing rates or the heartbeat and/or breathing rates of other connected system users.

7) Other guest sounds or frequencies may be broadcast to users or groups, such as the frequency of the earth, as a mean, or in certain specific locations, spiritual vortexes or hotspots, around the globe, either prerecorded or live.

8) One user may record a heartbeat and/or breathing rates session, and send the heartbeat and/or breathing recording to another as a "heart wish." The recipient would then listen to the recording and when the recipient's heartbeat and/or breathing rate are synchronized with recording, the device can record the playback session. The system users can then send their recording to each other to be able to respond to the other as an ongoing conversation over time but on the vital level.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty which characterize the invention are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

BRIEF DESCRIPTION OF THE DRAWINGS

FIGS. 11A, 11B, and 11C illustrate different views of an embodiment of a clamshell structure that can be used with the inventive stethoscope system.

FIG. 12 illustrates a perspective view of an enlarged view of an embodiment of the neck wrap component.

FIG. 13 illustrates a front view of a view of an embodiment of an ear piece and support wire.

DETAILED DESCRIPTION

Figure 1:
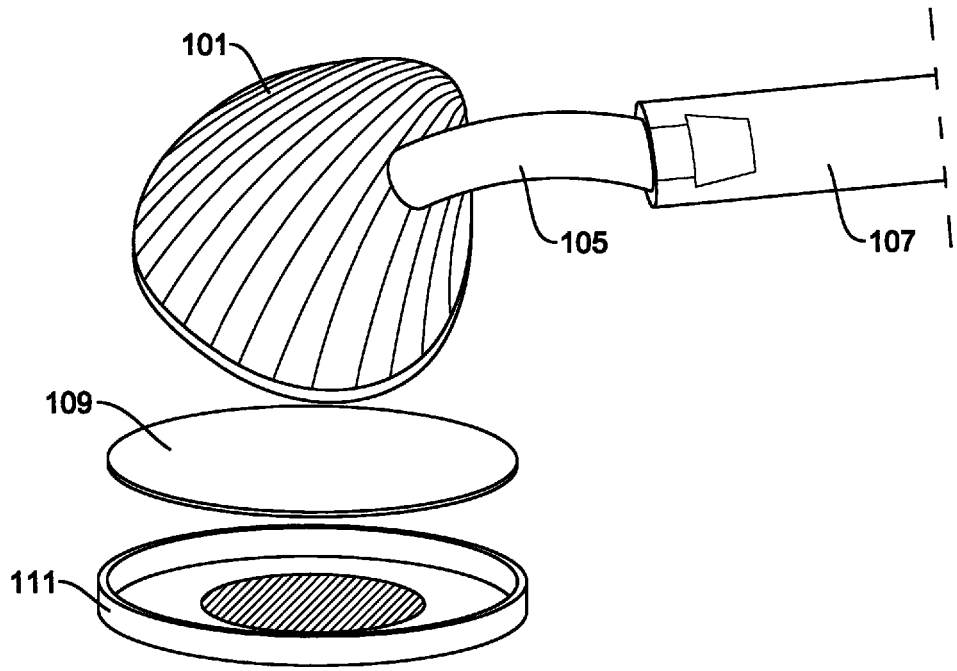
FIG. 1 illustrates a perspective view of an embodiment of a seashell chest piece that can have multiple possible diaphragms.

The present invention is directed towards a stethoscope system that can include various combinations of chest pieces, diaphragms, ear pieces, and electronic components that can allow users to share their heartbeats and breathing sounds through mechanical, electronic, and wireless communication means. With reference to FIG. 1, an embodiment of a stethoscope having a seashell shaped chest piece body 101 is illustrated. In this embodiment, a chest piece body 101 of the stethoscope can be made of a seashell or fabricated from rigid materials into a shell shape. The shell shaped body 101 can have a curved inner concave shape with a planar perimeter surface and a convex outer surface. In different embodiments, the shell body 101 can be made from or modeled on a Cardiidae family cockle bivalve mollusk such as: Kingdom Animalia, Phylum Mollusca, Class Bivalvia, Subclass Heterodonta, Order Cardiidae, and Super Family Cardiidae.

A tubular stem 105 can be attached to and can extend through the wall of the shell shaped body 101 so that the inner portion of the tubular stem connector 105 is open to the inner volume of the shell shaped body 101. The portion of the tubular stem connector 105 extending out of the shell shaped body 101 can be coupled to a tubing 107 that is then coupled to ear pieces (not shown). Various types of diaphragms 109, 111 can be attached to planar perimeter surface of the shell shaped body 101.

In an embodiment, the diaphragm 109 can be a thin heat shrink plastic that extends around the outer planar perimeter surface of the shell shaped body 101. When the shrink plastic diaphragm 109 is heated, the plastic sheet material will contract so that a perimeter edge of the plastic diaphragm 109 wraps over a perimeter portion of the outer convex surface of the shell body 101. The plastic diaphragm 109 can shrink to secure the plastic diaphragm 109 to the shell body 101 and form a gas tight seal with the shell body 101.

In other embodiments, the molded plastic snap-on diaphragm 111 can be a 3 dimensional structure that has a raised perimeter edge that can match or be slightly smaller than the perimeter portion of the outer convex surface of the shell body 101. The molded plastic snap-on diaphragm 111 can snap onto the planar perimeter surface of the shell body 101. The molded plastic snap-on diaphragm 111 can form a liquid tight seal with the shell body 101. The snap on design of the molded plastic diaphragm 111 can allow the diaphragm 111 to be easily replaced. The snap-on diaphragm 111 can be easily attached and detached from the shell body 101 which makes it easy to replace the snap-on diaphragm 111 if it is damaged, becomes dirty, or if a different diaphragm design is needed.

Figure 2:
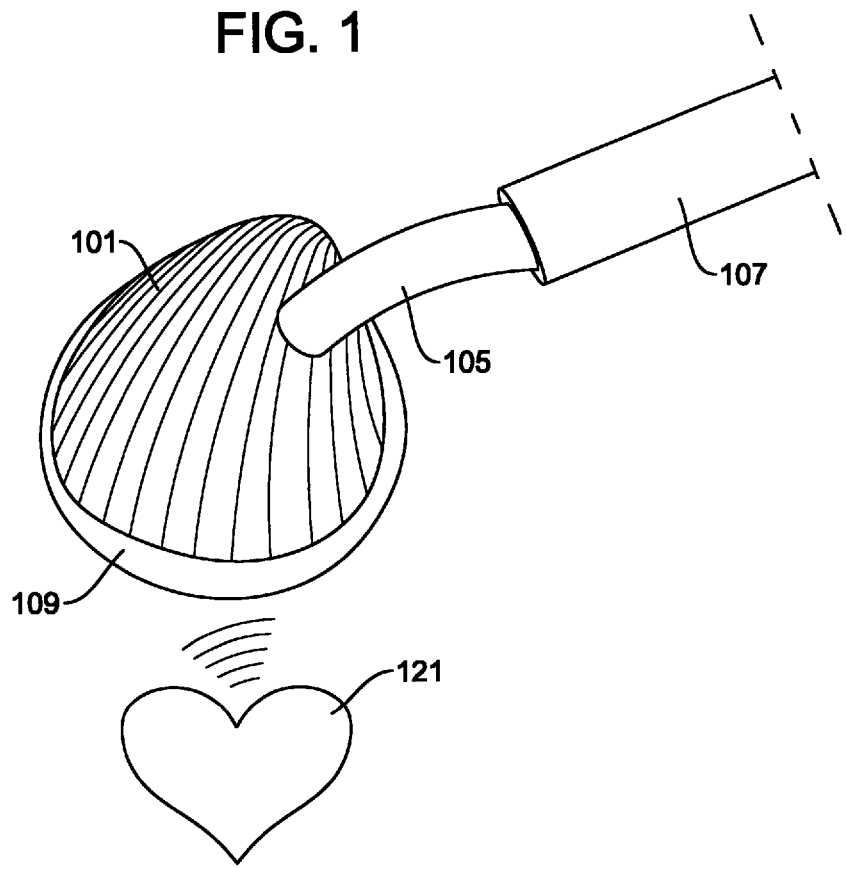
FIG. 2 illustrates a perspective view of a seashell chest piece with a diaphragm that can be used with the inventive stethoscope system.

With reference to FIG. 2, in an embodiment the shell body 101 can be coupled to a tubular stem connector 105 that is coupled to the elastic tubing 107 that is coupled to the hearing mechanism. The shell body 101 can have a hole in the convex surface and the tubular stem connector 105 can be coupled to the hole in the convex surface in the shell body 101. A hollow flexible tubing 107 can be coupled to the tubular stem connector 105 that is coupled to the hole in the convex surface of the shell body 101. The tubing 107 can be coupled to an audio mechanism that is heard by the users of the stethoscope. The user can hold the convex surface of the shell body 101 and press the diaphragm 109 against a surface of a chest for detecting a heartbeat from a heart 121. The diaphragm 109 can be made of a thin plastic material that can vibrate when placed over a heart 121. The movement of the chest can transmit a heartbeat audio signal through the diaphragm 109. The vibration can result in sound waves that travel through the shell body 101 and the tubing 107 coupled to the shell body to the audio mechanism. The user can listen to the heartbeat through the connected audio mechanism.

Figure 3:
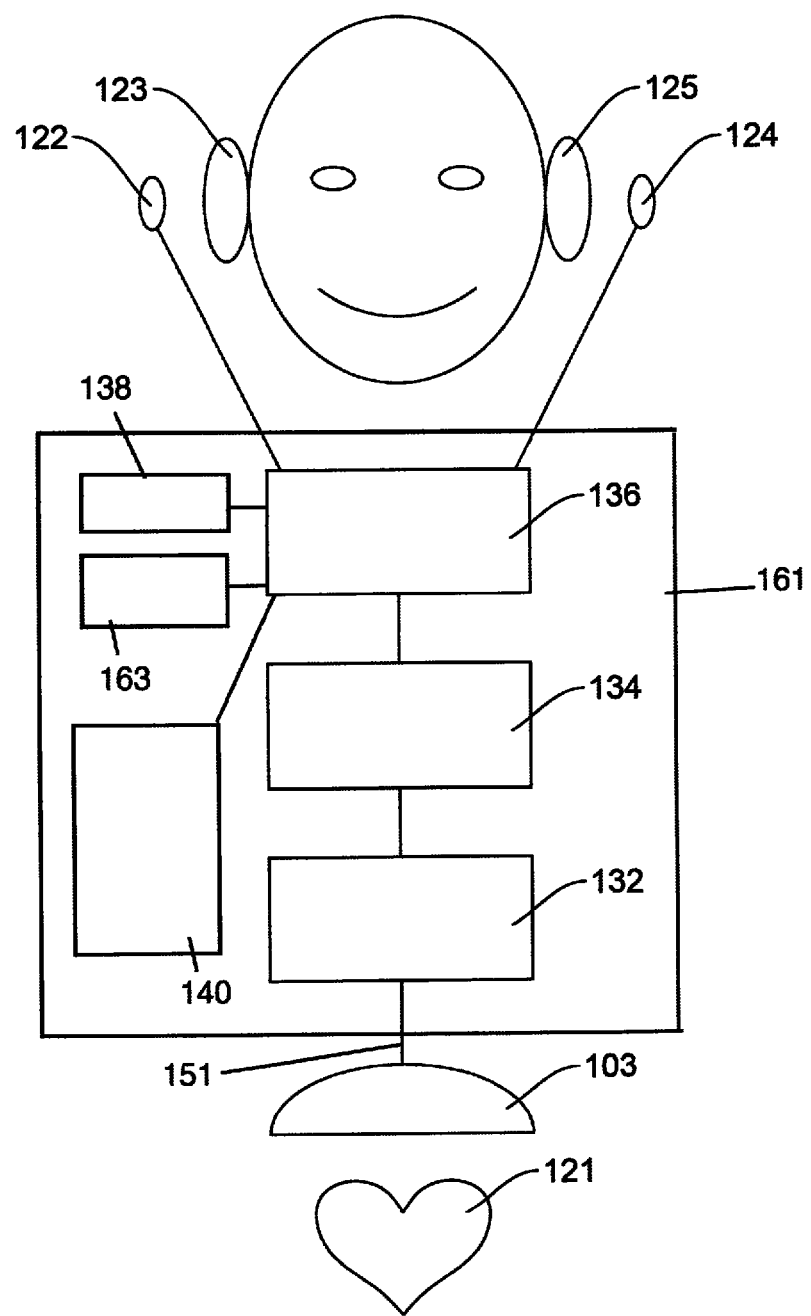
FIG. 3 illustrates an electronic embodiment of the inventive stethoscope system.

In some embodiments, the inventive system can also be configured with electronic components that can process the heartbeat and breathing output audio signals. FIG. 3 illustrates an embodiment of a heartbeat system having an electronic component assembly 161. In this embodiment, the stethoscope is used to detect and process heartbeat audio signals 131, 133 that are then transmitted to the user's two ears 123, 125. A microphone 132 can be coupled to the head or chest piece 103 of the stethoscope with tubing 151. In other embodiments, the microphone 132 can be built into the chest piece 103 and the microphone 132 can be connected to the amplifier 134 with a wired connection or a wireless radio frequency connection. The microphone 132 converts the audio heartbeat signal from a heart 121 into an electronic heartbeat signal that is transmitted to an amplifier 134 coupled to the chest microphone 132. The amplifier 134 can amplify the electronic heartbeat signal and transmit the amplified electronic heartbeat signal to a computer processor 136 through a wired connection. The processor 136 can transmit a normal heartbeat audio signal to a first ear output 122 that is heard by the first ear 123 and a second ear output 124 that is heard by the second ear 125. The processor 136 can transmit a heartbeat audio signal to the first ear output 122 and the second ear output 124 through wired or wireless radio frequency connections.

In some embodiments, the processor can also be coupled to a voice microphone 138, a visual display 140 for displaying visual information from the processor 136, and a transmitter or transceiver 163 for sending and/or receiving wireless signals. In some embodiments, the electronic components including but not limited to: the microphone 132, the amplifier 134, the computer processor 136, the voice microphone 138, visual display 140, and the transmitter or transceiver 163 can be incorporated into an electronic device on a printed circuit board and placed in a durable housing.

In some embodiments, FIG. 3 illustrates an embodiment of a binaural heartbeat system. The processor 136 can alter the frequency of the normal heartbeat audio signal and output the heartbeat as a second heartbeat audio signal to a second ear output 124. The second heartbeat audio signal can be heard by the second ear 125 that has a slightly different frequency and tone. When a user hears two tones one in each ear 123, 125 that have slightly different in frequencies, the listener's brain processes a beat at the difference of the frequencies. This brain processed beat is called a binaural beat. For example, a first heartbeat sound emitted by the first ear output 122 to the user's right ear 123 can have a heartbeat sound frequency of about 132 Hertz (Hz) and a second heartbeat sound emitted by the second ear output 124 to in the user's left ear 125 can be at a heartbeat sound frequency of about 121 Hz. The user's brain can gradually fall into synchronicity with the frequency difference which can be 11 Hz. Instead of hearing two different tones from the eat outputs 122, 124, a user can instead hear a frequency different tone at 11 Hz in addition to the two tones 132 Hz and 121 Hz in each ear 123, 125.

Binaural beats can be considered auditory illusions. For a binaural beat to work, the two tones emitted by the ear outputs 122, 124 may need to have frequencies that are both less than 1,000 Hz, and the difference between the two tones can't be more than 30 Hz. The tones also have to be listened to separately, one through each ear 123, 125. Binaural beats have been explored in music and are sometimes used to help tune instruments, such as pianos and organs. More recently, binaural beats have been connected to potential health benefits.

Figure 4:
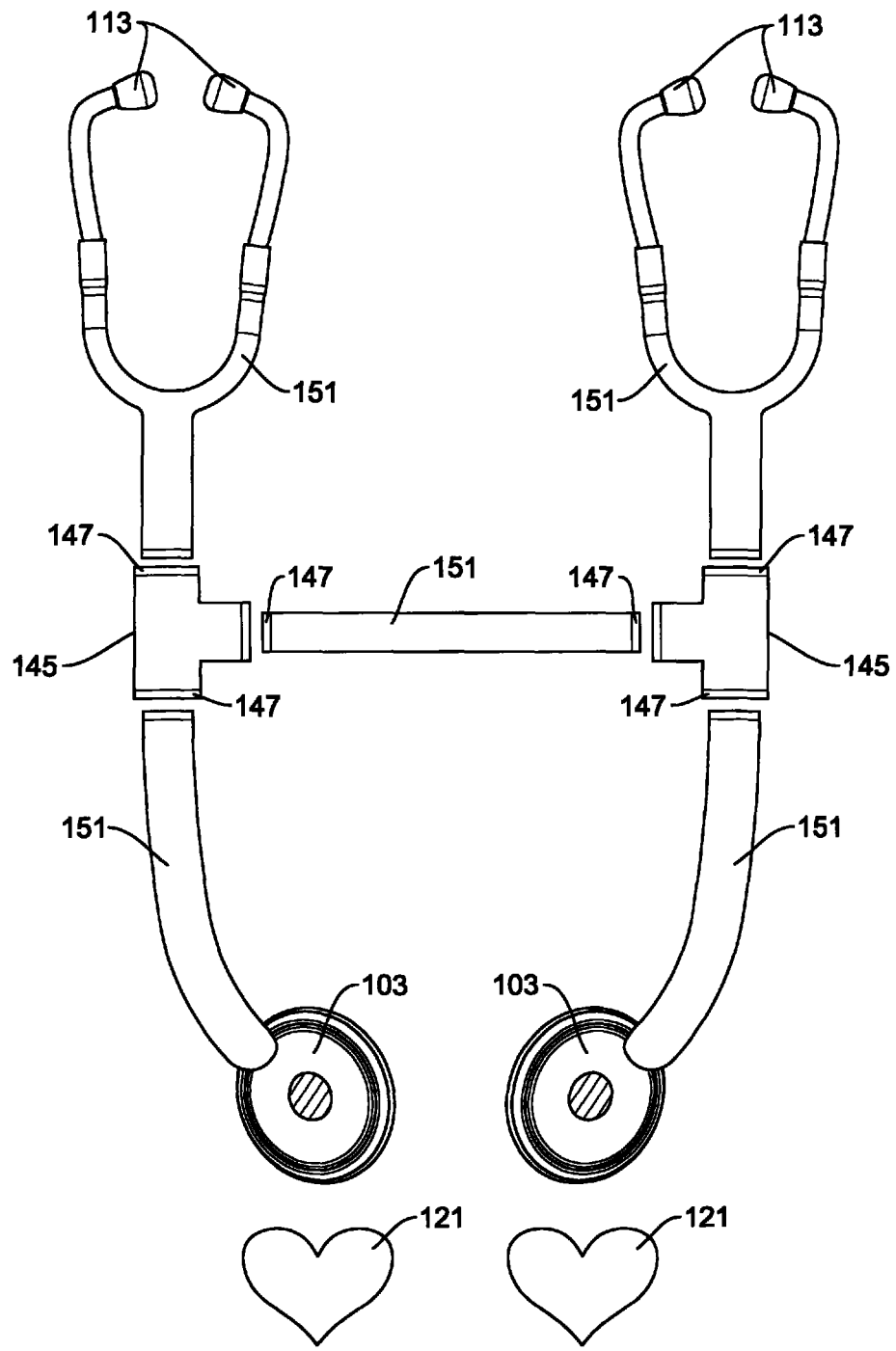
FIG. 4 illustrates a front view of a modular two user embodiment of the inventive stethoscope system.
Figure 5:
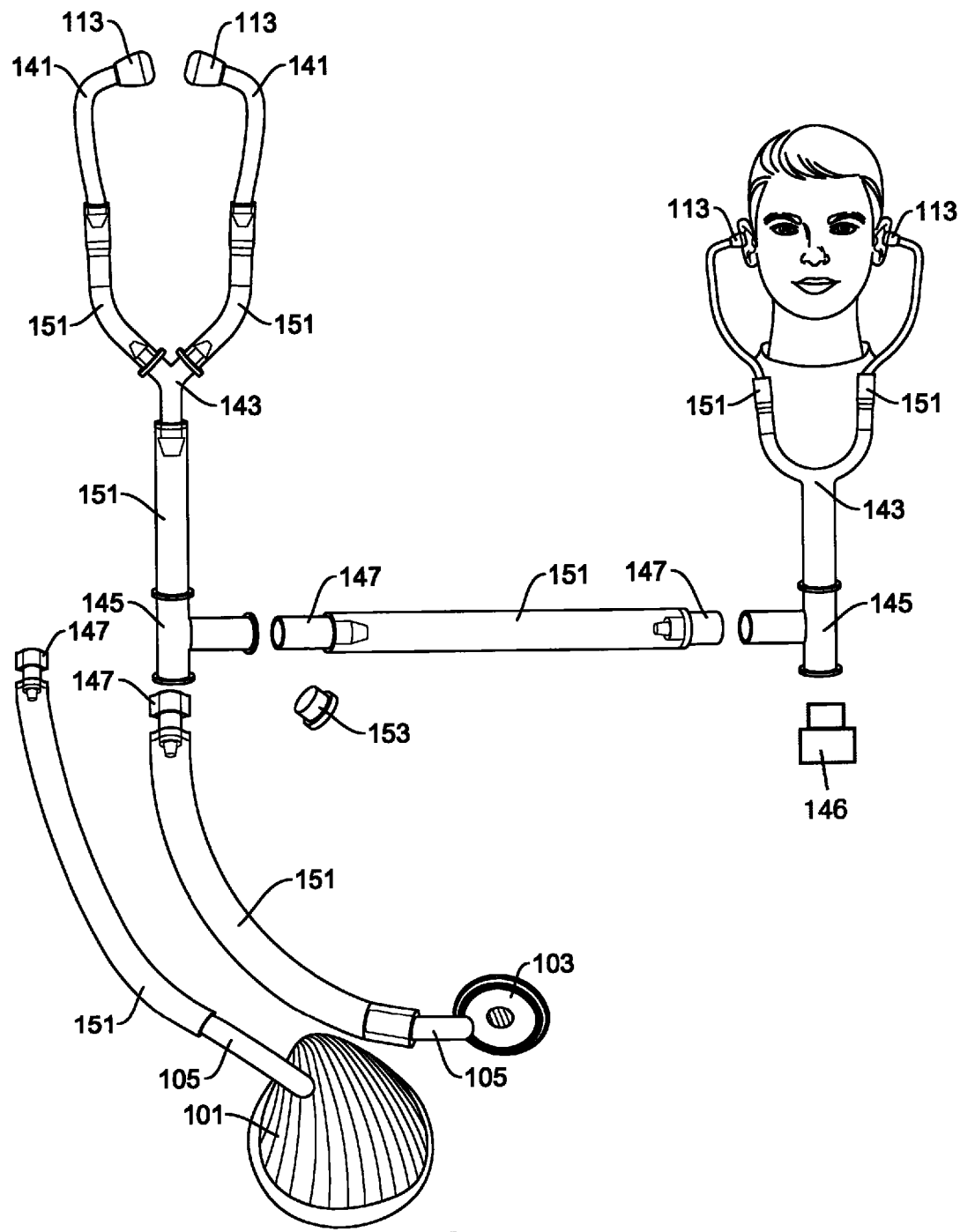
FIG. 5 illustrates a front view of a modular embodiment of the inventive stethoscope system with multiple possible chest pieces.

A study has shown that music can be used to relieve patient anxiety before a medical operation, and that audio embedded with tones that create binaural beats within the brain of the listener decreases subjective levels of anxiety in patients with chronic anxiety states. For example, pre-operative anxiety is common and often significant. Ambulatory surgery challenges our pre-operative goal of an anxiety-free patient by requiring people to be 'street ready' within a brief period of time after surgery. Music can be used successfully to relieve patient anxiety before a medical operation, and audio embedded with tones that create binaural beats within the brain of the listener can decrease subjective levels of anxiety in patients with chronic anxiety states. The anxiety levels were measured with the State-Trait Anxiety Inventory questionnaire and compared binaural beat audio (Binaural Group) with an identical soundtrack but without these added tones (Audio Group) and with a third group who received no specific intervention (No Intervention Group). Mean [95% confidence intervals] decreases in anxiety scores were 26.3% [19-33%] in the Binaural Group (p=0.001 vs. Audio Group, p<0.0001 vs. No Intervention Group), 11.1% [6-16%] in the Audio Group (p=0.15 vs. No Intervention Group) and 3.8% [0-7%] in the No Intervention Group. Binaural beat audio has the potential to decrease acute pre-operative anxiety significantly. A prospective, randomized, controlled study examining binaural beat audio and pre-operative anxiety in patients undergoing general anesthesia for day case surgery, Association of Anesthetists. Jul. 7, 2005. https://associationofanaesthetists-publications.onlinelibrary.wiley.com/doi/full/10.1111/j.1365-2044.2005.04287.x FIGS. 4 and 5 illustrate embodiments of multi user modular stethoscopes that can have quick connect fittings that allow users to add or remove stethoscope components. In FIG. 4, the illustrated embodiment of the modular stethoscope assembly has two separate stethoscopes that each have "T" connectors 145. Each individual stethoscope can have a diaphragm 109, chest pieces 103, tubing 151, a "T" connector 145, and a sound output 121. The two stethoscopes are coupled to each with tubing 151 that is coupled to the "T" connectors 145. The two users can place the diaphragms 109 and the chest pieces 103 over two hearts 121 of the two users. Sounds from the two hearts 121 are both transmitted through the diaphragms 109, the chest pieces 103, and the tubing 151 to the two sets of ear sound outputs 144 so that each user can hear both heartbeats.

In the illustrated embodiment, a horizontal tubing 151 connects the two stethoscopes. The connection tubing 151 can have quick release couplings 147 on the ends of the connection tubing 151 pieces. The length of the tubing 151 can be variable depending upon the application requirements. For example, for a mother and child, the tubing 151 length can be short because the mother will typically be holding the child. In contrast, if two adults are using the modular stethoscope assembly, the tubing 151 length can be longer because to allow the two adult users to be comfortably seated or standing with sufficient space between the two users.

In some embodiments, the ear piece sound outputs 144 can be simple plastic pieces having inner tubular structures that can be inserted into the users' ears. Alternatively, in other embodiments, the sound outputs 144 can be small electrical speakers that can transmit audio signals to the user's ears. In the electrical speaker embodiment, a microphone can convert the heartbeat sound into electrical heartbeat signals and then the electrical heartbeat signals can be amplified and transmitted to electrical headphones, earbuds, or wireless sound outputs devices. In some other embodiments, the electrical heartbeat signals can be output as radio frequency signals that can be transmitted to wireless headphones or earbuds.

With reference to FIG. 5, another embodiment of a modular stethoscope assembly is illustrated that has more connection components. In the illustrated embodiment, the modular stethoscope assembly can have two ear piece sound outputs that are coupled with tubing 151 to a chest piece. The ear piece sound outputs 144 can each have ear pieces 113 that are coupled to "L" shaped connectors 141. Flexible tubing 151 is coupled to the "L" shaped connectors 141. The flexible tubing 151 are both coupled to the upper legs of the "Y" shaped connector 143. The lower leg of the "Y" shaped connector is coupled to a flexible tubing 151 that is coupled to a "T" connector 145. The side and lower legs of the "T" connectors 145 can have quick connection attachment points. The side connection of the "T" connector 145 is coupled to a quick connection coupling 147 that is attached to a horizontal connection tubing 151 that connects the two ear piece sound outputs. The lower leg of the right side "T" connector 145 can be closed with a plug 146 that can be inserted into the lower leg of the right side "T" connector 145.

The modular stethoscope assembly can have multiple chest piece assemblies so that the users can select a desired chest piece from a plurality of chest pieces. A first chest piece assembly can have a circular disk shaped chest piece 103 that is attached to a tubular coupling 105. A tube 151 is attached to the tubular coupling 105 on one end and a quick release coupling 141 on the opposite end. A second chest piece assembly can have a seashell shaped chest piece body 101 that is attached to a tubular coupling 105. A tube 151 is attached to the tubular coupling 105 on one end and a quick release coupling 141 on the opposite end. The quick release coupling 141 can be easily coupled or removed from the lower leg of the "T" connector 145.

The ear sound outputs 144, "T" connector 145, and the chest pieces 103 can be assembled by the users into various desired configurations. For example, the stethoscope can be built with: 1) a single chest piece 103 and diaphragm 109 coupled with tubes 151 to two user ear sound outputs 144, 2) two chest pieces 103 and two diaphragms 109 coupled to single user ear sound output 144, 3) two chest pieces 103 and two diaphragms 109 coupled together and to two ear sound outputs 144, etc. If a coupling such as the "T" connectors 145 have unused connection points. Plugs 146 can be used to plug the unused opening connection of the "T" connectors 145.

Figure 6:
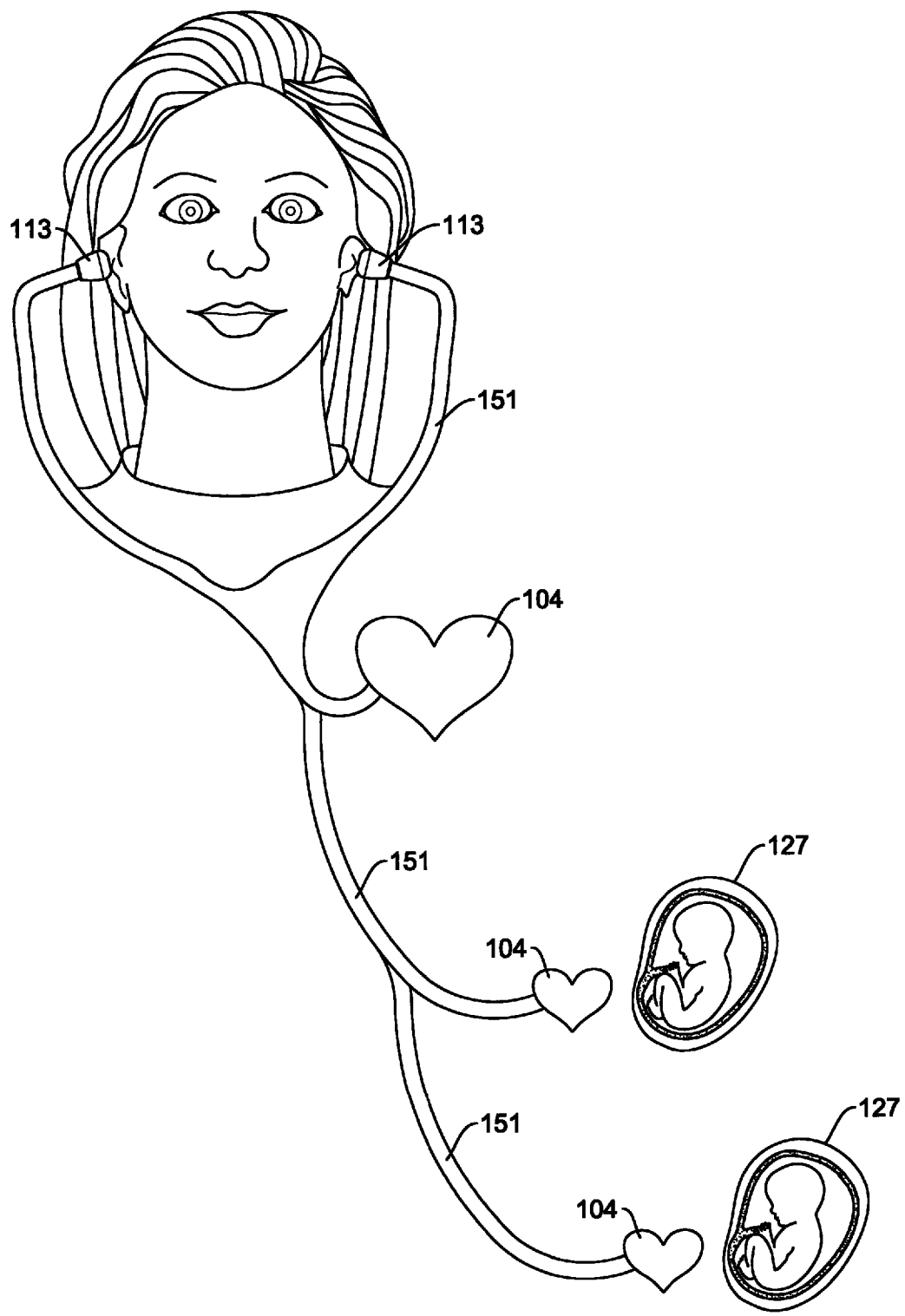
FIG. 6 illustrates a front view of an embodiment of the inventive stethoscope system with three chest pieces.

With reference to FIG. 6, a stethoscope assembly can be configured to have three chest pieces 104 that each have a diaphragm. In prior illustrated embodiments, the chest pieces can be circular or shell shapes. In this illustrated embodiment, the chest pieces 104 can be heart shaped. The three chest pieces 104 are coupled to a single ear output having ear pieces 113 that are coupled to left and right tubing 151 pieces. The left and right tubing 151 pieces can be connected at a "Y" connection 143. Another tubing 151 can extend from the lower leg of the "Y" connection 143. The three chest pieces 104 are coupled to the tubing 151. A pregnant mother can place one of the diaphragms on her chest and two diaphragms on her abdomen. Heartbeat sounds from the mother and twin fetuses can travel from the diaphragms through the tubing 151 and tubing connections to the ear pieces 113. The mother can use the stethoscope assembly to hear her own heartbeat as well as the heartbeats of twin fetuses.

Figure 7:
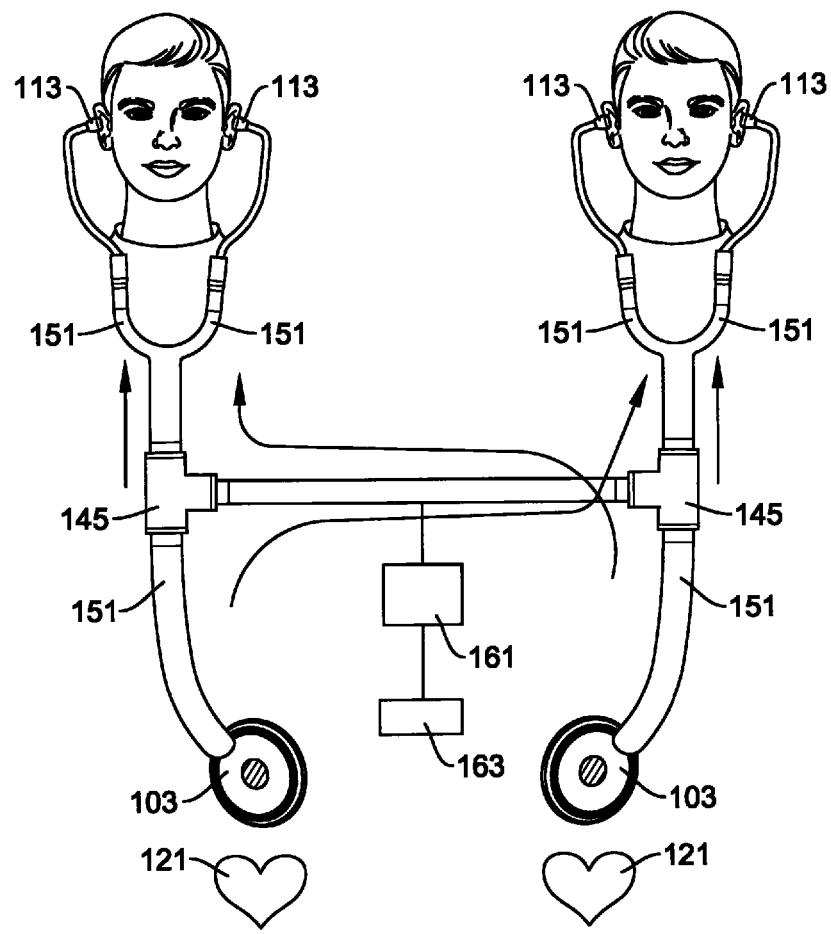
FIGS. 7 and 8 illustrate a front view of two user embodiments of the inventive stethoscope system.
Figure 8:
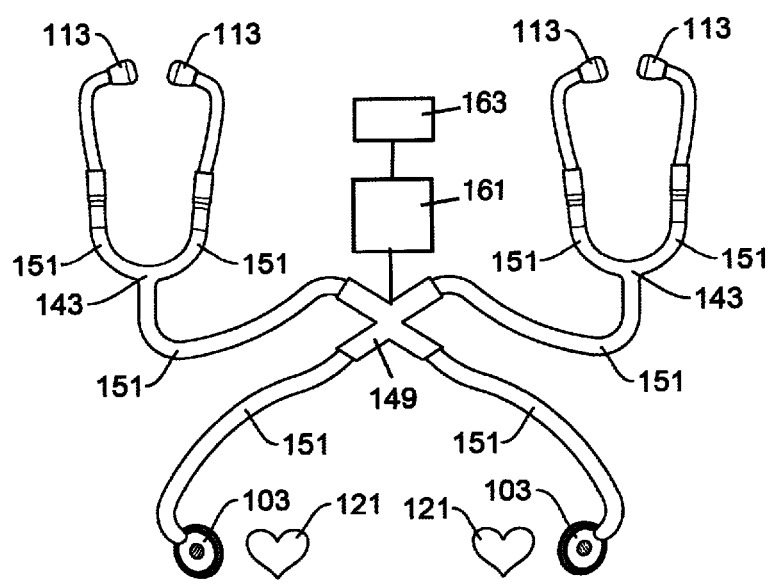

FIGS. 7 and 8 illustrate other embodiments of the modular stethoscope assembly, a two user linked heartbeat/breath synchronization stethoscope is illustrated. The embodiment illustrated in FIG. 7 is similar to the embodiment illustrated in FIG. 4. The modular stethoscope assembly can have two chest pieces 103 and two diaphragms placed over the users' hearts 121 for detecting the heartbeats and breathing of the users. The two chest pieces 103 are coupled to two sets of ear outputs 113 that are connected with tubing 151 and couplings 145. The ear outputs 113 can be worn or heard by the two system users. In other embodiments, additional tubing 151, couplings 145, chest pieces 103, and ear outputs 113 can be connected to the modular stethoscope assembly to expand the assembly to accommodate more system users.

FIG. 8 is also similar to the embodiments illustrated in FIGS. 4 and 7. The modular stethoscope assembly can have two chest pieces 103 for detecting heartbeats and two diaphragms placed over the users' hearts 121 for detecting the heartbeats and breathing of the users. The two chest pieces 103 are coupled to tubing pieces 151, an "X" shaped coupling 149, and "Y" shaped couplings 143 to two sets of ear outputs 113. In other embodiments, additional tubing 151, "X" shaped coupling 149, "Y" shaped couplings 143, chest pieces 103, and ear outputs 113 can be connected to the modular stethoscope assembly to expand the assembly to accommodate more system users.

The modular stethoscope assemblies can allow two users to simultaneously listen to the heartbeats and breathing of the two users. Because the users can listen to the both users' heartbeats and breathing rates, the users can use these audio sounds to attempt to synchronize their heartbeats and breathing rates. The users can be close proximity to each other so that they can talk with each other to made adjustments to their heartbeats and breathing rates.

In an embodiment, an electronic component assembly 161 can be coupled to a tube 151 of the stethoscope assembly. The electronic component assembly 161 can be coupled to the connecting tubing 151 that is between the two "T" connectors 145 so that the heartbeats and breathing sounds are transmitted to the heartbeats and breathing microphone. The electronic component assembly 161 can include various electrical components including but not limited to: a computer processor, a heartbeat and breathing microphone, a voice microphone, amplifiers, an audio output such as a speaker, and a visual display such as light emitting diodes (LED) displays, liquid crystal displays (LCD) or any other visual display. The heartbeats and breathing sounds can be received through the heartbeat and breathing microphone of the electronic component assembly 161. The heartbeat and lung breathing audio signals can be converted into electrical signals that can then be transmitted to an amplifier to amplify the heartbeat and lung breathing audio signals that can then be processed by the computer processor of the electronic component assembly 161.

The computer processor of the electronic component assembly 161 can analyze the heartbeat and lung breathing electrical signals to distinguish the heartbeat data and lung breathing data that have different frequencies. The computer processor can then determine the heart rates and breathing rates of each of the system users. The heartbeat and lung breathing rates can be output by the computer processor as audio signals to a speaker or output by the computer processor as visual data as on the visual display. The speaker can be coupled to the connecting tubing 151 that is between the two "T" connectors 145 so that the audio signals from the computer processor can be transmitted to the system users through the ear outputs 113.

The users may need instructions for synchronization and the computer processor of the electronic component assembly 161 can transmit synchronization instructions that can be heard by the users through the two sets of ear outputs 113. For example, the processor 163 can be configured with a memory of a target heart rate range and a target breathing rate range for the users. The target heart rate and breathing rate can be based on the age and health of the system users.

The heart rate can be proportional to the breathing rate so a heart rate can be increased with faster breathing and slowed with slower breathing. The processor can determine the user's heart rate that is closest to the target heart rate. The processor can then provide audio or visual instructions to the speaker and/or visual display for the user whose heart rate is furthest from the target heart rate, to adjust his or her heart rate by increasing or decreasing the breathing rate. For example, if a first user has a heart rate that is in the target heart rate range and a breathing rate that is also at the target breathing rate this user data is detected by the processor. The second user can have a heart rate that is above the target heart rate and this out of target heart rate is also detected by the processor. In response to the out of target heart rate, the processor can output instructions to the second user to breathe more slowly to reduce the second user's heart rate to the speaker and/or visual display.

Once the processor detects that the second user's heart rate is within the target heartbeat rate range, the processor can inform the users that their heart rates are both within the target range. The processor can then emit instructions to the users to attempt to synchronize their heart rates and their breathing rates. The processor can detect continue to detect the heart rates and the processor can determine when the heart rates are synchronized. When heart rate synchronization is detected, the processor can emit a signal to the users to inform them that their heart rates are synchronized. The processor can emit a signal to inform the users through the speaker and/or visual display when their heart rates are no longer synchronized. In an embodiment, the processor can start timing the duration of the heart rates synchronization. The users can then attempt to set a synchronization duration record and the users can record their prior synchronization durations.

The electronic component assembly 161 can be coupled to a transmitter or transceiver 163 that can transmit and/or receive signals from networks and other sources. For example, the transmitter or transceiver 163 can be used to transmit data from the computer processor to the internet and other computing devices so that other people can listen to the heartbeat and/or breathing synchronization described above. The transceiver 163 can also allow internet connected users to participate in the described heartbeat and/or breathing synchronization. In some embodiments, the voices of the users can be transmitted through the voice microphone of the electronic component assembly 161 so that the internet connected users can hear the verbal communications of the stethoscope users. The computer processor can also transmit heart rate and/or breathing data described above through the transmitter or transceiver 163 to the internet connected users. For example, people using the stethoscope system illustrated in FIG. 3 can participate in the described synchronized heartbeat and breathing activities.

Figure 9:
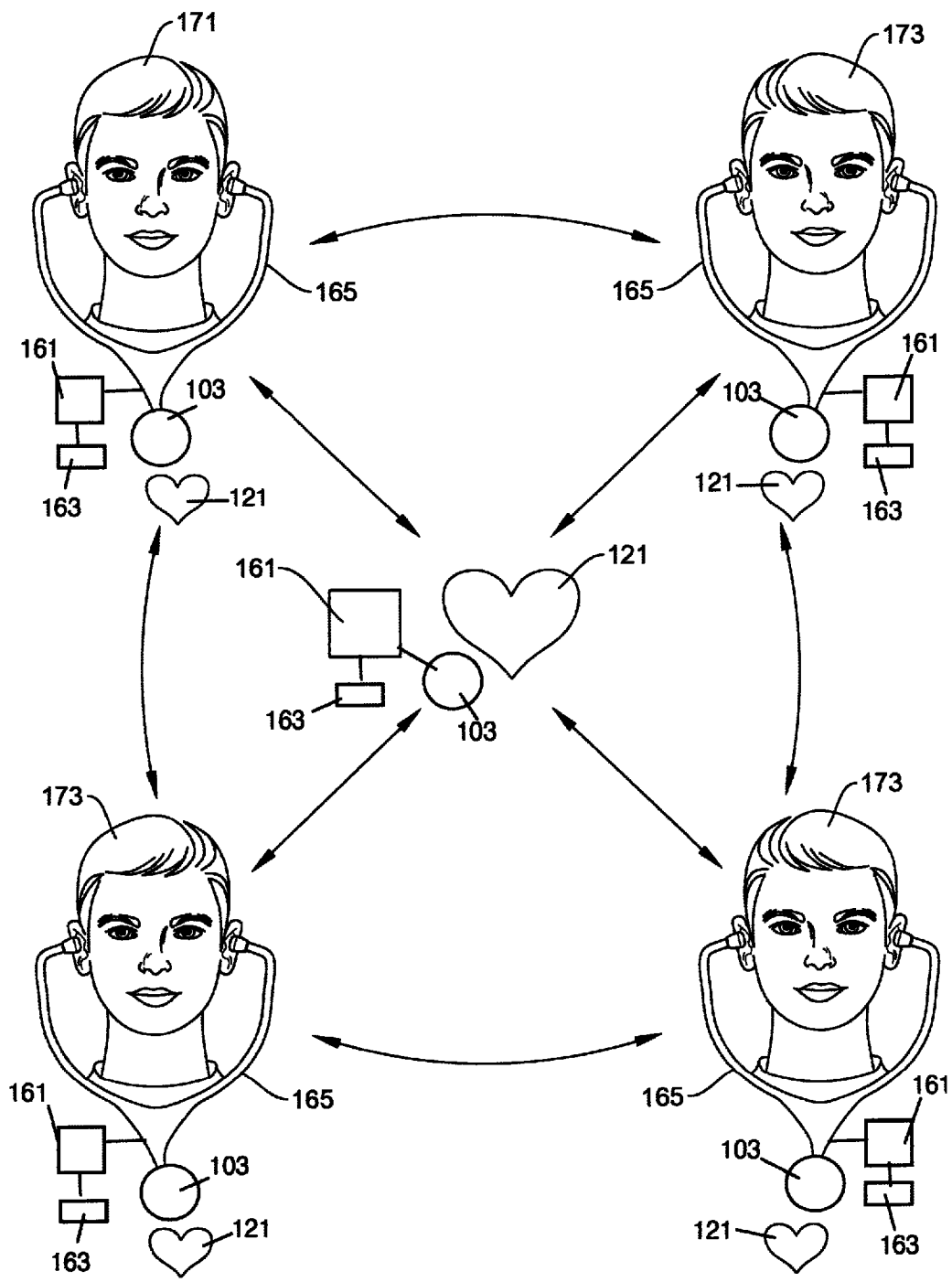
FIG. 9 illustrates an electronic multiple user embodiment of the inventive stethoscope system.

With reference to FIG. 9, a diagram of a heartbeat synchronization group is illustrated that includes four users 171, 173. In an embodiment, one of the users can be a "host" user 171 who can set the target heart rate and breathing rate. The host user 171 can attempt to hold this heart rate and breathing rate during the synchronization process. The other users 173 can adjust their heart rates and possibly breathing to be synchronized to the host heart rate and breathing. Each of the users 171, 173 can listen to a stethoscope apparatus 165 having ear pieces and chest pieces 103 for at least one person. The chest piece 103 can be placed over the heart 121 of the user. The electronic component assembly 161 can be coupled to the stethoscope apparatus 165 that has the components described above with reference to FIG. 3. The user's heartbeat and breathing data can be transmitted from the electronic component assembly 161 through a transmitter or transceiver 163 to other system users.

In some embodiments, each of the users 173 can hear their own heartbeats and lung breathing as well as the heartbeats and lung breathing of the host users 171. The users 173 can attempt to alter their own heartbeats and breathing rate to match the heartbeat and breathing of the host 171. The processors in the electronic component assembly 161 can assist the users 173 through various methods. The processors can inform the users 173 of the differences in the heartbeat and breathing rate to the host and then provide instructions for altering the user's heartbeat rate.

In an embodiment, the system can electronically alter the heartbeat and breathing sounds so that the sounds of the users' heartbeat and breathing rates that are synchronized with the heartbeat and breathing rates of the host 171 can be louder than the unsynchronized heartbeat rate of the other users 173, so that unsynchronized heartbeat users 173 can more easily determine that their heartbeat rates are unsynchronized. The unsynchronized user 173 can detect the unsynchronized breathing and heart rate and the user can make adjustments. Alternatively, the unsynchronized user 173 can receive instructions so that the unsynchronized users' 173 heartbeat rates can be adjusted and synchronized with the heart rate host 171.

In an embodiment, the system configuration can include electronic stethoscope systems 165 that can be worn by each system user. The electronic stethoscope systems 165 can be similar to the device illustrated in FIG. 3. Each electronic stethoscope systems 165 can include: a microphone, an amplifier, a processor, a transceiver, and an audio output device. The microphones can convert the audio heartbeat signals into electronic heartbeat signals that can be transmitted to amplifiers coupled to the microphone and delivered to headphones of all of users. In other embodiments, the described heartbeat synchronization can be performed through the internet to the users can be remotely located from each other.

Figure 10:
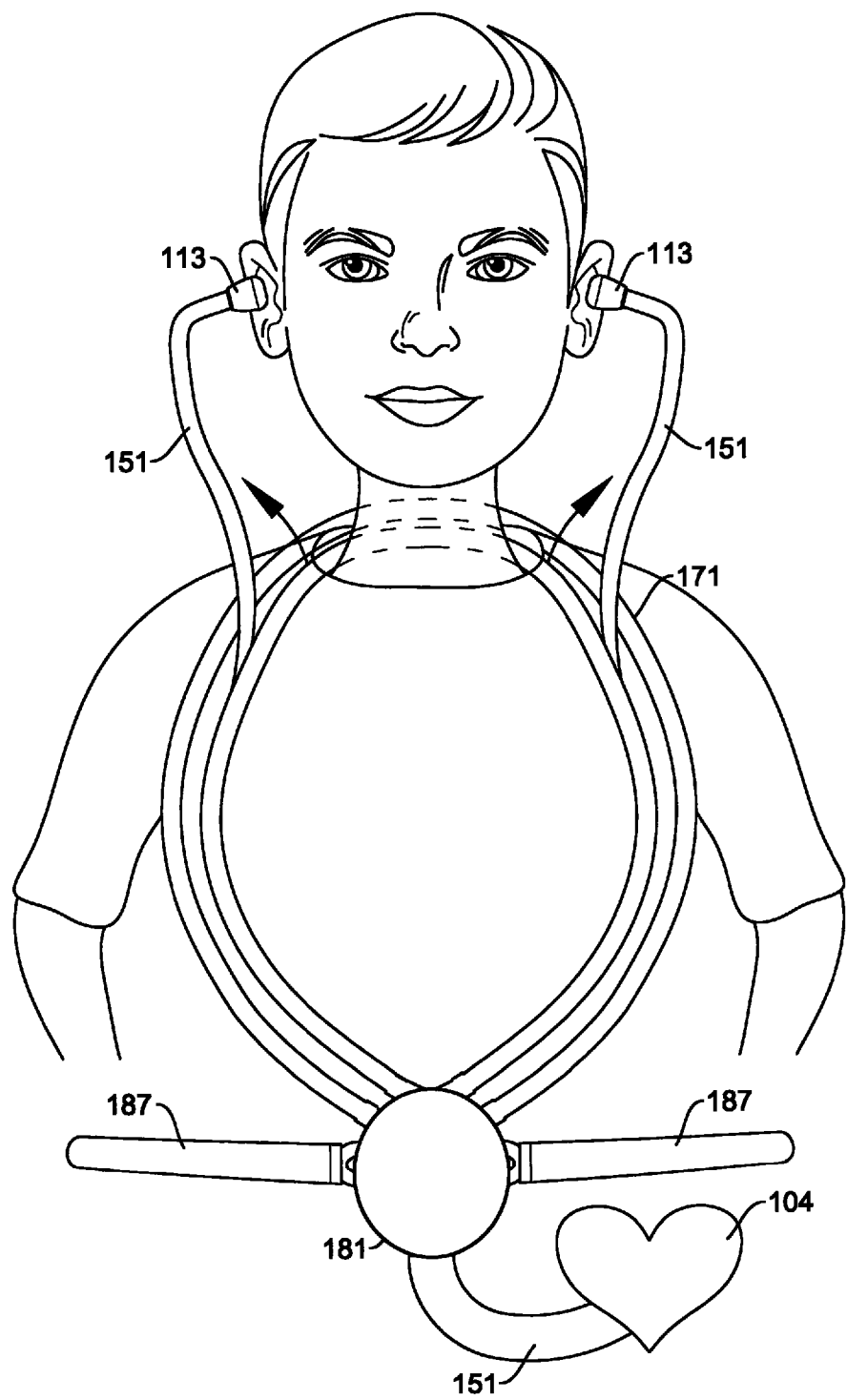
FIG. 10 illustrates a front view of an embodiment of the inventive stethoscope system having a chest strap and neck wrap body connection design.

FIG. 10 illustrates an embodiment of a stethoscope apparatus that can components that be secured to the body of the system user so that the user does not need to manually hold the chest piece in place. In the illustrated embodiment, the inventive stethoscope can be a sleeping version that can be securely worn while sleeping. In this embodiment, the tubing 151 and ear pieces 113 can be made of a flexible silicone material without any metal or rigid components that can be rigid and uncomfortable when the user moves in bed while sleeping.

The embodiment of a stethoscope apparatus can have a clamshell structure 181 can have an integrated diaphragm and chest piece for the stethoscope can be attached to the chest area of the user with a releasable adhesive and/or a strap 187 that is wrapped around the user's chest and adjusted in tension so that the diaphragm will remain in comfortable contact with the user's chest. This can be useful when the user is sleeping. The ear pieces 113 can also be coupled to the user's ears with releasable adhesive. In this embodiment, the user can listen to his or her own heartbeat which can result in more relaxation and deeper sleeping. The clamshell structure 181 can also have a manifold that can allow additional tubes 151, diaphragms 111, and chest pieces 104 to be attached. In the illustrated embodiment, an additional tube 151, diaphragm 111, and chest piece 104 is attached to the bottom of the clamshell structure 181. These added components can be used to allow a pregnant mother to listen to her fetus.

The inventive stethoscope can have a necklace embodiment that can include a loop housing 172 and a chest strap or straps 187 that allow the user to secure the diaphragm 111 and the chest piece 104 over the heart area of the user. The ear pieces 113 can also be secured to the ears so that they are not removed when the user moves. The loop housing 172 can have a "C" shaped cross section. When the user is not using the stethoscope, the ear pieces can be placed into groove of the open tubing of the loop housing 172. In an embodiment, the loop housing 172 of the necklace stethoscope can be concealed in an ornamental fabric that is placed over a cover loop housing 172 that can be an open tubing structure. The ornamental fabric can be any suitable material. For example, the ornamental fabric can be an ornamentally printed silk that can cause the stethoscope to look like a scarf.

FIG. 12 illustrates an enlarged view of a portion of an embodiment of the loop housing 172 having the "C" shaped cross section. The tubing 151 and a connected flexible wire 173 can be placed in the loop housing 172. The user can remove the tubing 151, flexible wire 173, and ear pieces when the stethoscope is being used. When the stethoscope is being used, the tubing 151, flexible wire 173, and ear pieces can be placed into the "C" shaped cross section of the loop housing 172 so that these components are protected. FIG. 13 illustrates the flexible wire 173 attached to the tubing 151 and the ear piece 113 at the proximal end of the tubing 151. The wire 173 can allow the user to bend the tubing 151 to any desired curvature. Once bent, the wire 173 and tubing 151 will maintain the bent shape. This feature can be helpful to position the ear pieces 113 at comfortable positions during use.

FIGS. 11A, 11B, and 11C illustrate additional views of the clamshell structure 181. FIG. 11A illustrates a side perspective view of the closed clamshell structure 181. FIGS. 11B and 11C illustrate side views of the opened clamshell structure 181. The clamshell structure can include a hollow volume storage housing that can be used to house, store, and protect the diaphragm 182 and a manifold 145. The clamshell structure 181 can have a hinge 185 to allow the clamshell structure 181 to be opened or closed. When the clamshell structure 181 is closed, the clamshell structure 181 forms a sealed structure that functions as a chest piece. The diaphragm 182 can be built into the housing with the diaphragm structure having an anchor structure that can be releasably coupled to the housing storage anchor. The housing can have a front piece and a rear piece that are coupled with a hinge. When the diaphragm structure is stored, the clamshell structure 181 housing can be closed to protect the diaphragm 182. The sound vibrations form the diaphragm 182 can travel into a hole in the manifold 145 that can have openings that can extend to holes in the clamshell structure 181. As illustrated in FIG. 10, the tubes 151 and ear pieces 113 can be coupled to a top connection point of the manifold 145 and a tube 151, chest piece 104, and diaphragm 111 can be attached to a bottom connection point of the manifold 145. A side connection point of the manifold 145 can be available if additional devices need to be connected to the clamshell structure 181 or the side connection point of the manifold 145 can be plugged if no additional device is needed.

A nub 183 can be mounted to the clamshell structure 181 housing on a surface that is opposite the diaphragm 182. The nub 183 can be a circular structure that is coupled to the clamshell structure 181 housing with a smaller diameter cylinder. The nub 183 can be used to secure the clamshell structure 181 housing to the straps 187 or a strap mount mechanism. The nub 183 can be easily and securely attached to and removed from the straps 187.

In some embodiments, the clamshell structure 181 can be large enough to function as a storage container for all of the illustrated components. When the stethoscope is used, the ear pieces can be removed from the clamshell structure 181 and placed in the user's ears. The clamshell structure 181 housing can be opened and the diaphragm and chest piece structure can be removed and set up as the user desires. When all of the needed components are removed and assembled, the clamshell structure 181 housing can be closed. The tubing 151 can pass through a hole in the clamshell structure 181 housing between the two housing pieces and the diaphragm 182 can be placed on the chest of the user.

Figure 14A:
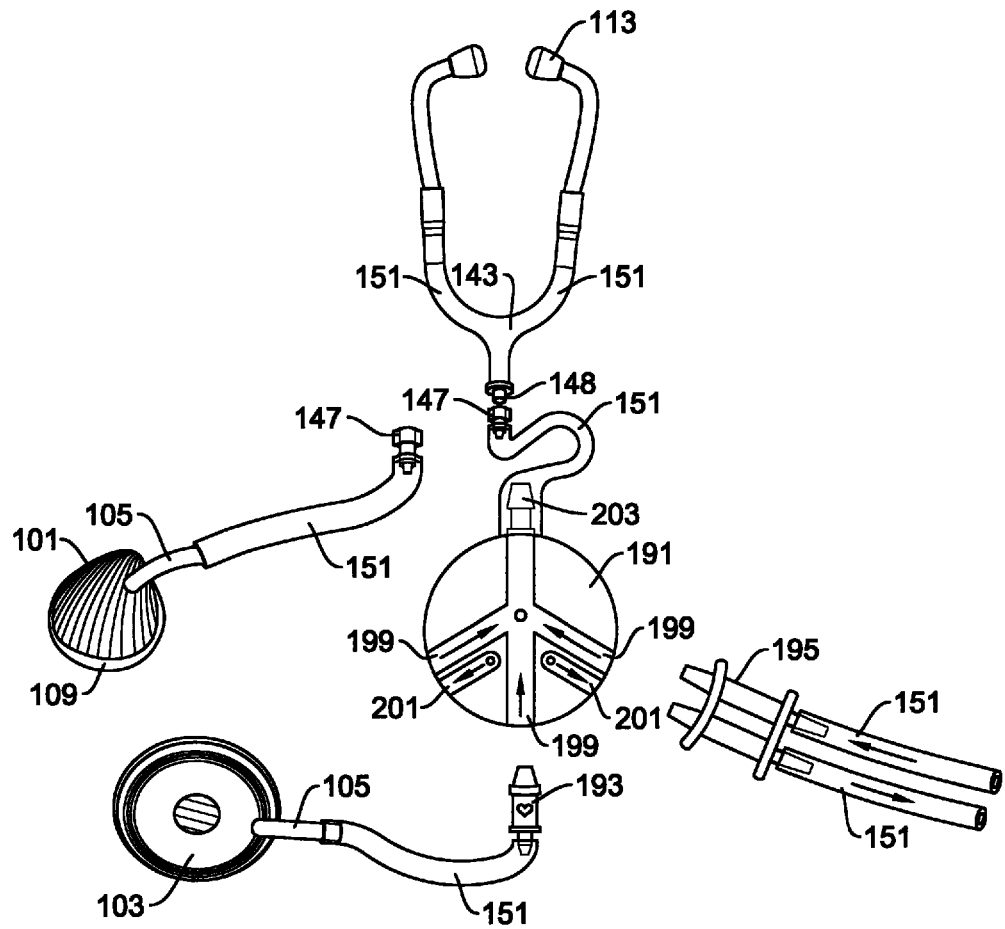
FIG. 14A illustrates a front view of a modular embodiment of the inventive stethoscope system with a heart module.

FIG. 14A illustrates another embodiment of the stethoscope apparatus that has a number of interchangeable components including: an ear piece assembly, a single stethoscope assembly, a heart module assembly, and input/output tubing. The modular design of the stethoscope apparatus allows various components to be assembled in many different assemblies that can accommodate a plurality of users. In the illustrated embodiment, the ear piece assembly having the ear pieces 113, tubing 151, Y connector 143, and quick connector 148 can be connected to any heartbeat and breathing sound source. For example, the ear piece assembly can be connected to a single stethoscope having a chest piece 101, diaphragm 109, connector 105, tubing 151, and quick connector 147. Alternatively, the ear piece assembly can be connected to a heart module 191 through tubing 151 and a quick connector 147. The heart module 191 can have an integrated diaphragm, internal flow paths, a tube coupling 203, sound input flow paths 199, and sound output flow paths 201. A center bottom sound input flow path 199 of the heart module 191 can be coupled to a single stethoscope having a chest piece 103, diaphragm, connector 105, tubing 151, and single tube heart module connector 193. Lower side sound input flow path 199 of the heart module 191 can be coupled to a shared heartbeat and breathing sound input and output having a double tube heart module connector 195 coupled to sound input and output tubing 151. The sound input and output tubing 151 can also be coupled to other heart modules and/or other ear piece assemblies that are not shown in this drawing.

Both the single tube heart module connector 193 and the double tube heart module connector 195 can be made of an elastic material and have conical couplings that have outer diameters that fit within the inner diameters of the input flow path 199 and the output flow path 201. The single tube heart module connector 193 and the double tube heart module connector 195 can be pressed into the heart module 191 to connect additional components. The compression and friction of the conical couplings within the inner diameters of the input flow path 199 and the output flow path 201 can securely hold the single tube heart module connector 193 and the double tube heart module connector 195 to the heart module 191. The single tube heart module connector 193 and the double tube heart module connector 195 can also easily be pulled from the heart module 191 to separate any components.

Figures 14B, 14C:
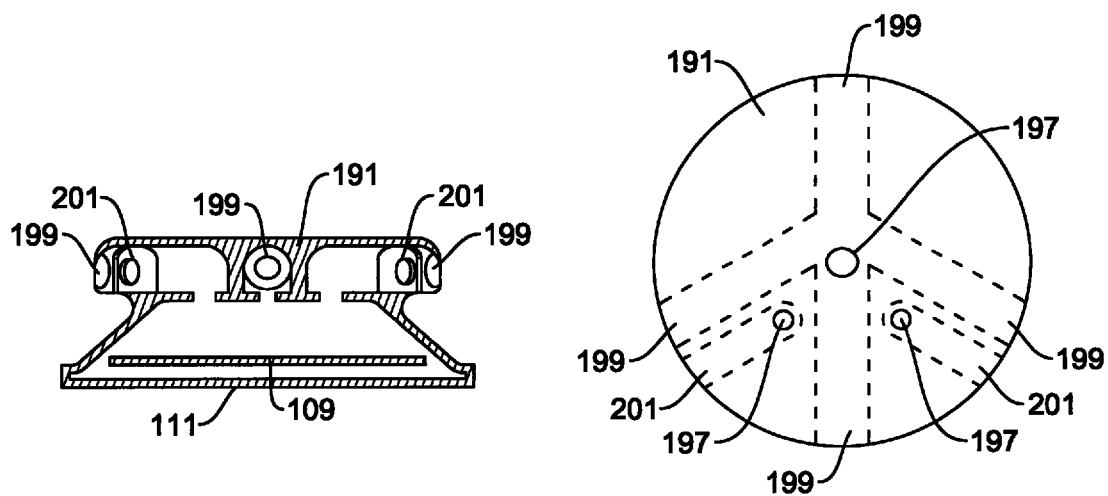
FIG. 14B illustrates a side cross section view of an embodiment of a heart module that can be used with the inventive stethoscope system.
FIG. 14C illustrates a bottom cross section view of an embodiment of a heart module that can be used with the inventive stethoscope system.

FIG. 14B illustrates a cross section side view of the heart module 191 and FIG. 14C illustrates a cross section bottom view of the heart module 191. The heart module 191 can be a circular hollow structure that include a diaphragm 111 on one side of the heart module 191 and an open interior volume. Internal passageways, sound input flow paths 199, and sound output flow paths 201 can be in the heart module 191 on an opposite side from the diaphragm 111. Holes 197 can connect the open interior volume to the internal passageways of the heart module 191. The input flow path 199 and the output flow path 201 extend to the outer diameter surface of the heart module 191. In some embodiments, the sound detected by the diaphragm of the heart module 191 can be altered by adding a fluid filled structure 109 to the diaphragm 111.

FIGS. 14A and 14C illustrate a heart manifold 191 that includes a center flow path that can extend through a center line of the heart manifold 191. A center hole 197 at the center of the heart manifold 191. The center hole 197 passes through to the air volume adjacent to the diaphragm. Heartbeat and breathing sounds flow from the diaphragm through the center hole 197 to the center flow path up to the ear piece assembly so the user can hear their own heartbeat and breathing sounds The center flow path has a lower connection point that can be coupled to other stethoscopes sounds. The center flow path also intersects with two diagonal flow paths that extend out the sides of the heart manifold 191 that receive other stethoscopes sounds. If each input is coupled to a stethoscope, the ear piece assembly can hear four users' heartbeat and breathing sounds.

The heart manifold 191 also has two output flow paths 201 that extend into the heart manifold 191 and connect with holes 197 that pass through to the air volume adjacent to the diaphragm. Heartbeat and breathing sounds from the diaphragm flow through the center holes 197 to the two output flow paths 201 through tubing and the connected ear piece assemblies so that other connected users can hear the first user's heartbeat and breathing sounds.

Figure 15:
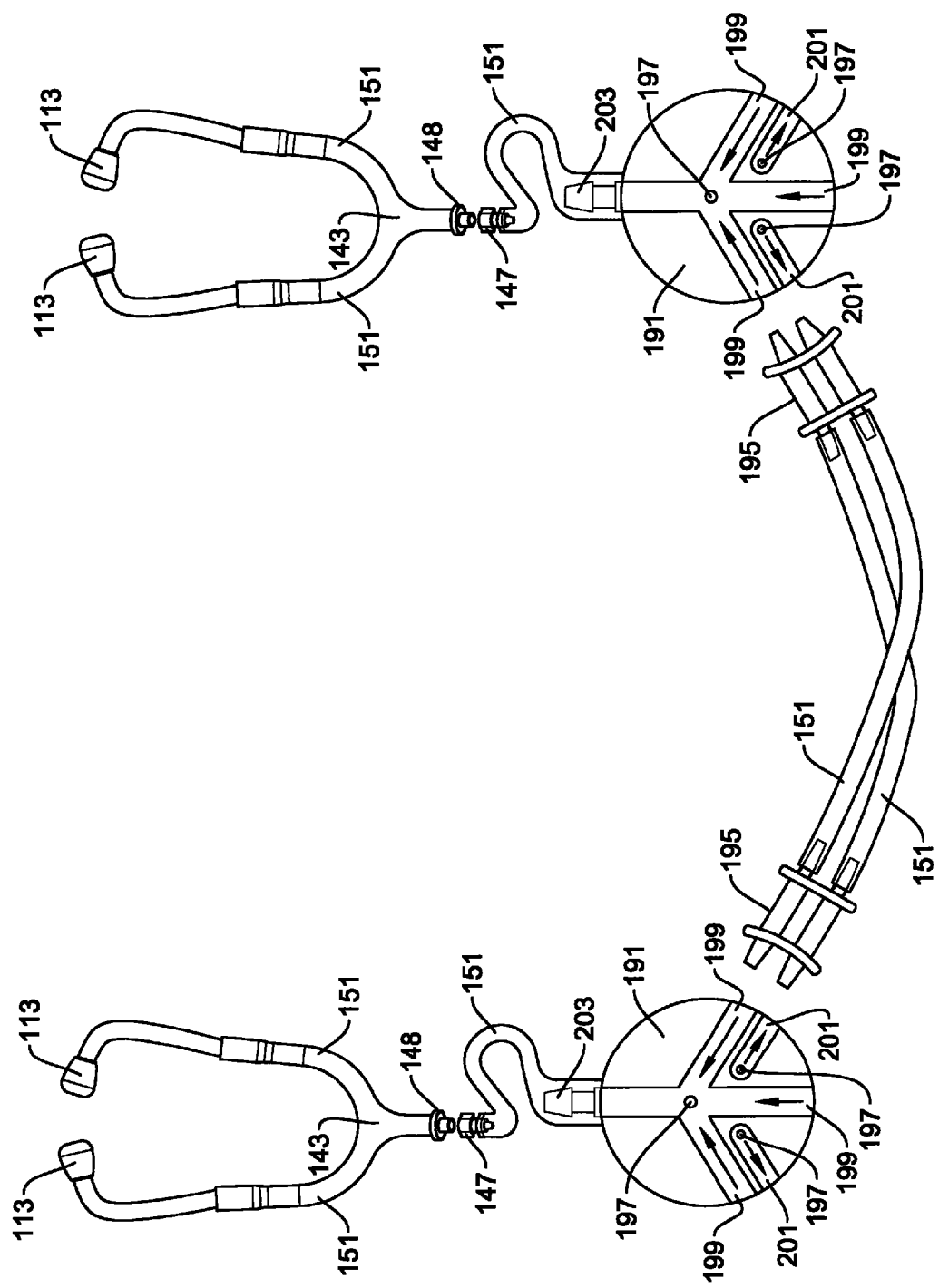
FIG. 15 illustrates a front view of a modular two user embodiment of the inventive stethoscope system with heart modules.
Figure 16:
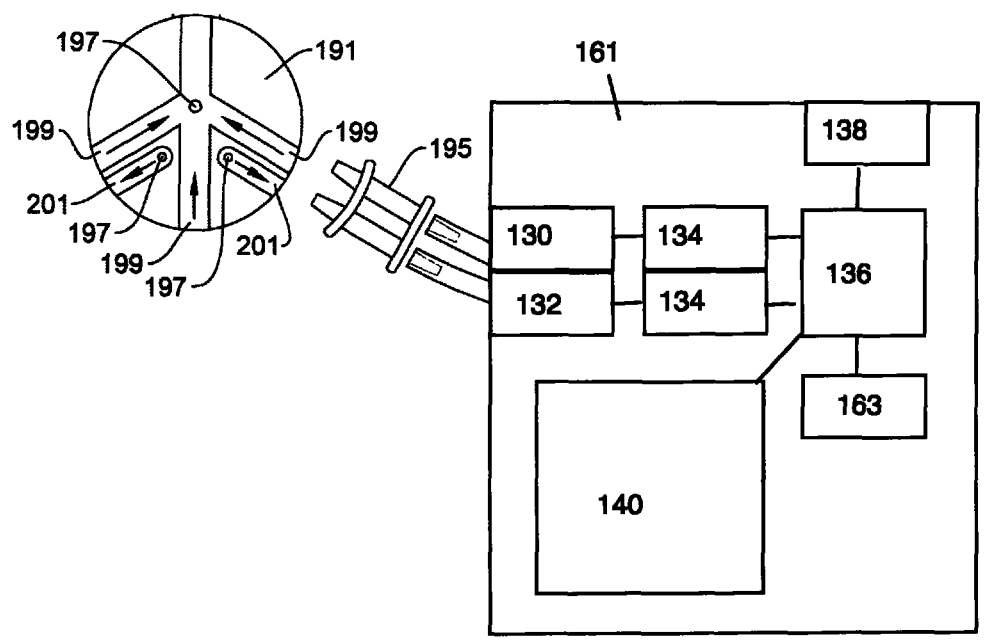
FIG. 16 illustrates an embodiment of a heart module and an electronic assembly that can be coupled to the heart module.

FIG. 15 illustrates an embodiment of a double user heart module stethoscope system. In the illustrated embodiment, ear piece assemblies are coupled to heart module assemblies with quick connectors 147, 148. These assemblies were described above with reference to FIG. 14A. The heart modules 191 can be connected to each other with double input/output tubing 151 with the output flow path 201 of the left heart module 191 coupled to the input flow path 199 of the right heart module 191. The input flow path 199 of the left heart module 191 coupled to the output flow path 201 of the right heart module 191. Additional stethoscope components can be connected to the heart modules 191. However, when other components are not connected the open input 199 and outputs 201 on the heart module 191 should be plugged with plugs 146.

In this configuration, the two users can each place the ear pieces 113 in their ears and place the heart modules 191 on their chests. The heartbeat and breathing sounds of the left user can travel from the left heart module 191 diaphragm through the hole 197 to the left ear piece assembly. The heart and breathing sounds of the left user can also travel from right output 201 of the left heart module 191 through the left coupling 195, tubing 151, right coupling 195, right heart module 191 to the right ear piece assembly so the right user can listen to the heartbeat and breathing sounds of the left user. Similarly, the heartbeat and breathing sounds of the right user can travel from the right heart module 191 diaphragm through the hole 197 to the right ear piece assembly. The heart and breathing sounds of the right user can also travel from left output 201 of the right heart module 191 through the right coupling 195, tubing 151, left coupling 195, left heart module 191 to the left ear piece assembly so the left user can listen to the heartbeat and breathing sounds of the right user. The right and left users can then attempt to synchronize their heart rates and then their breathing as described above.

As discussed above, in some embodiments, the stethoscope apparatus can be coupled to an electronic component assembly 161. In some embodiments, the electronic component assembly 161 can include is but not limited to: the microphone 132, the amplifier 134, the computer processor 136, the voice microphone 138, visual display 140, and the transmitter or transceiver 163 can be incorporated into an electronic device on a printed circuit board and placed in a durable housing. The heartbeat and breathing output from the system can be transmitted from the tubing 151 and received by the microphone 132. A speaker 130 can be coupled to the amplifier 134 and processor 136. The speaker 130 can output heartbeat and breathing audio signals from other users as well as any audio information from the processor 136. The electronic component assembly 161 can also include a processor 136 that can be coupled to a voice microphone 138, a visual display 140 for displaying visual information from the processor 136, and a transmitter or transceiver 163 for sending and/or receiving wireless signals.

In some embodiments, the stethoscope apparatus can be configured to alter the sound of the heartbeats. For example, the stethoscope can be configured to simulate the sounds of the heartbeat and/or breathing through a liquid such as amniotic fluid that can simulate the sounds of a fetus in liquids in a womb. This altered sound can be preferable and/or more comforting to families or parents who want a pregnancy like experience.

Figure 17:
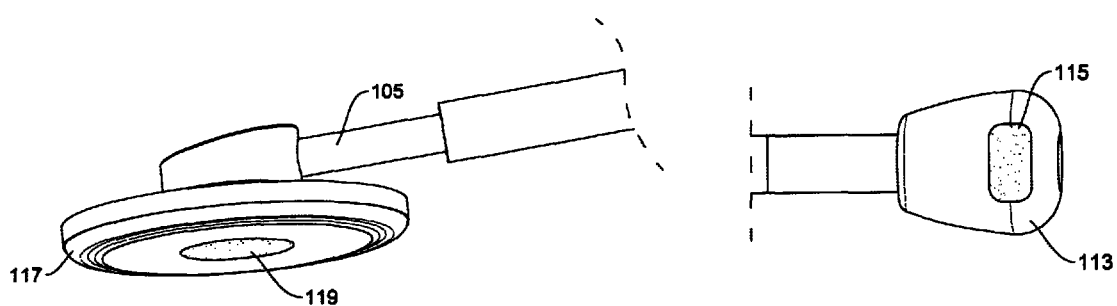
FIG. 17 illustrates an embodiment of a chest piece having a fluid filled diaphragm.

FIG. 17 illustrates a diaphragm structure 117 that can have an integrated structure that contains an internal volume 119 that is filled with a liquid. The diaphragm structure 117 can be placed on the chest and the heartbeat and/or breathing sound waves can vibrate both the diaphragm structure 117 and the internal volume 119 filled with the liquid. The vibration of the internal volume 119 filled with the liquid can then transmit a more muffled sound out of the diaphragm structure 117 to the ear pieces 113. The transmission of sound through the fluid in the diaphragm structure 117 and the internal volume 119 filled with the liquid can result in a heartbeat and/or breathing that sounds like it is coming from the womb.

Figure 18:
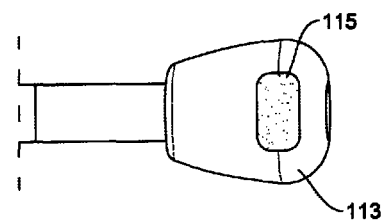
FIG. 18 illustrates an embodiment of an ear piece having a fluid filled body.

With reference to FIG. 18, the ear piece 113 can include an elastic structure 115 that surrounds a volume filled with a fluid. The elastic structure 115 can be placed between the tubing 151 and the ear sound outlet of the ear piece 113. Heartbeat and/or breathing sound waves can enter the tubing 151 and then travel through the fluid in the elastic structure 115. The vibration of the fluid can then transmit a more muffled sound out of the ear pieces 113. The transmission of sound through the fluid in the elastic structure 115 can result in a heartbeat and/or breathing that sounds like it is coming from the womb.

In other embodiments, a microphone can be used to convert the audio signals into electrical signals that can be processed by a processor to muffle or add the liquid effect to the heartbeat and/or breathing sounds. The processed electrical signals can then be transmitted to a headphone that is placed on or in the user's ears.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like. Therefore, the above description and illustrations should not be construed as limiting the scope of the invention, which is defined by the appended claims.

The present disclosure, in various embodiments, includes components, methods, processes, systems, and/or apparatus substantially as depicted and described herein, including various embodiments, subcombinations, and subsets thereof. Those of skill in the art will understand how to make and use the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease, and/or reducing cost of implementation. Rather, as the following claims reflect, inventive aspects lie in less than all features of any single foregoing disclosed embodiment.

What is claimed as invention is:

1. A multi-user modular stethoscope apparatus comprising:
    a first heart module having a first sound input flow path and a first sound output flow path wherein the first sound input flow path and the first sound output flow path are separate internal passageways within the first heart module;
    a first diaphragm coupled to the first heart module;
    a first double tube heart module connector connected to the first sound input flow path of the first heart module and the first sound output flow path of the first heart module;
    a first ear piece flexible tubing coupled to the first heart module;
    a first ear piece coupled to the first ear piece flexible tubing;
    a second heart module having a second sound input flow path and a second sound output flow path wherein the second sound input flow path and the second sound output flow path are separate and parallel internal passageways within the second heart module;
    a second diaphragm coupled to the second heart module;
    a second double tube heart module connector connected to the second sound input flow path and the second sound output flow path of the second heart module;
    a first flexible tubing coupled to the first double tube heart module connector and the second double tube heart module connector; and
    a second flexible tubing coupled to the second heart module and the first heart module wherein the first flexible tubing is adjacent and parallel to the second flexible tubing;
    wherein the second heart module is physically separated from the first heart module, the first heart module is adapted to receive first heart sounds from a first user, and the second heart module is adapted to receive second heart sounds from a second user.

2. The apparatus of claim 1, further comprising:
    a third heart module having a third sound input flow path and a third sound output flow path wherein the third sound input flow path and the third sound output flow path are separate internal passageways within the third heart module;
    a third diaphragm coupled to the third heart module;
    a third double tube heart module connector connected to the third sound input flow path and the third sound output flow path of the third heart module; and a third flexible tubing coupled to the third heart module connector and the first heart module;

wherein the third heart module is physically separated from the first heart module and the second heart module, and the third heart module is adapted to receive third heart sounds from a third user.

3. The apparatus of claim 2, further comprising:

a fourth heart module having a fourth sound input flow path and a fourth sound output flow path wherein the fourth sound input flow path and the fourth sound output flow path are separate internal passageways within the fourth heart module;

a fourth diaphragm coupled to the fourth heart module; and a fourth flexible tubing coupled to the fourth heart module and the first heart module;

wherein the fourth heart module is physically separated from the first heart module, the second heart module, and the third heart module, and the fourth heart module is adapted to receive fourth heart sounds from a fourth user.

4. The apparatus of claim 1, wherein the first ear piece includes an elastic structure filled with a liquid.

5. The apparatus of claim 1, wherein the first diaphragm includes an elastic structure filled with a liquid.

6. The apparatus of claim 1, further comprising:

a microphone coupled to the first heart module for converting audio signals into electrical signals;

an amplifier coupled to the microphone for amplifying the electrical signals;

a processor for processing the electrical signals;

a transmitter for transmitting the electrical signals;

receivers for receiving the electrical signals; and an audio output coupled to each of the receivers for converting the electrical signals into the audio signals and emitting the audio signals.

7. The apparatus of claim 1, further comprising:

an elastic structure filled with a fluid in the first heart module.

8. The apparatus of claim 1 further comprising:

a plug placed in a connection point of the first heart module.

* * * * *